(12) United States Patent
Kim

(10) Patent No.: US 11,612,759 B2
(45) Date of Patent: Mar. 28, 2023

(54) MEDICAL SKIN WRINKLE REDUCTION DEVICE USING RRSS LASER IRRADIATION METHOD AND WRINKLE REDUCTION METHOD OF USING SAME

(71) Applicant: Youin Kim, Cheongju-si (KR)

(72) Inventor: Youin Kim, Cheongju-si (KR)

(*) Notice: Subject to any disclaimer, the term of this patent is extended or adjusted under 35 U.S.C. 154(b) by 0 days.

(21) Appl. No.: 16/930,953

(22) Filed: Jul. 16, 2020

(65) Prior Publication Data

US 2021/0060352 A1    Mar. 4, 2021

(30) Foreign Application Priority Data

Aug. 27, 2019  (KR) .................. 10-2019-0105443

(51) Int. Cl.
| | | |
|---|---|---|
| *A61N 5/06* | (2006.01) | |
| *G16H 20/40* | (2018.01) | |
| *G16H 40/67* | (2018.01) | |
| *A61N 5/00* | (2006.01) | |
| *A61N 5/067* | (2006.01) | |

(52) U.S. Cl.
CPC .......... *A61N 5/0616* (2013.01); *G16H 20/40* (2018.01); *G16H 40/67* (2018.01); *A61N 5/067* (2021.08); *A61N 2005/007* (2013.01); *A61N 2005/0632* (2013.01); *A61N 2005/0642* (2013.01); *A61N 2005/0644* (2013.01)

(58) Field of Classification Search
CPC .......... A61N 5/0616; A61N 2005/007; A61N 5/067; A61N 2005/0644
See application file for complete search history.

(56) References Cited

U.S. PATENT DOCUMENTS

| | | | | |
|---|---|---|---|---|
| 2010/0241110 A1* | 9/2010 | Solomon | .............. | H05B 39/044 |
| | | | | 606/9 |
| 2018/0214208 A1* | 8/2018 | Kim | ..................... | A61B 18/203 |

FOREIGN PATENT DOCUMENTS

| | | |
|---|---|---|
| KR | 10-0698868 B1 | 3/2007 |
| KR | 10-0779954 B1 | 11/2007 |
| KR | 10-0820164 B1 | 4/2008 |
| KR | 10-0938378 B1 | 1/2010 |
| KR | 10-2014-0140393 A | 12/2014 |
| KR | 10-2014-0140395 A | 12/2014 |

(Continued)

*Primary Examiner* — Allen Porter
*Assistant Examiner* — Skylar Lindsey Christianson
(74) *Attorney, Agent, or Firm* — Novick, Kim & Lee PLLC; Jae Youn Kim

(57) ABSTRACT

A medical skin wrinkle reduction device using an RRSS laser irradiation method is proposed to reduce skin wrinkles and minimize tissue damage. The device includes: a main body having a mounting groove provided in an upper portion thereof, a tablet computer being attached to and detached from the mounting groove, and comprising signal transmission and reception parts exchanging signals with the tablet computer, and a microcomputer controlling an output of a laser beam; a handpiece comprising: a laser oscillation part generating the laser beam; an optical part emitting the laser beam as parallel light; a laser scanner controlling an irradiation position of the laser beam transmitted from the optical part; a laser pattern part having movement coordinate values set therein such that moving direction of the laser beam has a regular pattern; a tablet computer having functions of inputting data in a touch screen method and displaying a screen.

4 Claims, 7 Drawing Sheets

(56) References Cited

FOREIGN PATENT DOCUMENTS

| KR | 2014140395 A | * 12/2014 | ............. A61B 18/20 |
| KR | 10-1558948 B1 | 10/2015 | |
| KR | 10-1574951 B1 | 12/2015 | |
| KR | 10-1824460 B1 | 2/2018 | |
| WO | 2014-193029 A1 | 12/2014 | |

* cited by examiner

20

MEDICAL SKIN WRINKLE REDUCTION DEVICE USING RRSS LASER IRRADIATION METHOD AND WRINKLE REDUCTION METHOD OF USING SAME

CROSS REFERENCE TO RELATED APPLICATION

The present application claims priority to Korean Patent Application No. 10-2019-0105443, filed Aug. 27, 2019, the entire contents of which is incorporated herein for all purposes by this reference.

BACKGROUND OF THE INVENTION

Field of the Invention

The present invention generally relates to a medical skin wrinkle reduction device using a random regular shot spray (RRSS) laser irradiation method, whereby skin wrinkles are reduced and tissue damage is minimized. More particularly, the present invention relates to a medical skin wrinkle reduction device using an RRSS laser irradiation method for reducing skin wrinkles and minimizing tissue damage by securing the cooling time and maximum cooling of irradiated points therebetween due to the regular irradiation of a laser beam and a regular pattern formed thereby in a skin treatment process in which the laser beam irradiates the skin so that wrinkles are evenly smoothed throughout the treatment area and skin burns are prevented.

Description of the Related Art

Currently, various research on a laser irradiating the skin with a laser beam has been conducted, and various laser treatment techniques are also being developed.

Medical laser treatment techniques using lasers are used for various purposes such as preventing hair loss, promoting hair growth, skin peeling, skin regeneration, whitening, wrinkle reduction, spot removal, and freckle removal, etc.

Laser treatment is a method in which the entirety of a treatment area is treated, and light energy is transmitted to the entire treatment area from epidermis to a dermal layer. In this method, the skin is widely treated, but severe pain in the treatment area and many side effects may be caused due to high risk of the high energy transmission of the light energy.

In addition, as illustrated in FIG. 1, according to a conventional Fraxel laser, the linear irradiation of the skin by a laser beam is performed while the cooling of space between irradiated points is performed. However, positions in which wrinkles are not smoothed may occur, and skin burns may be caused due to the phenomenon of the laser beam focused on a specific position.

Conventional laser treatment methods have been applied in various forms. In the Fraxel laser in US as an example of the methods, laser beams emitted from a laser scanner are emitted in one direction while being maintained to be spaced apart by a predetermined interval from each other.

However, according to such a method, the laser beam is repeatedly emitted while being moved in one direction. Accordingly, before an area on which earlier laser beam is emitted is cooled, another laser beam irradiates the area adjacent thereto, whereby a cooling effect is lowered, and the decrease of post-inflammatory hyperpigmentation (PIH) and delayed tanning (DT) is difficult.

In a conventional technology illustrated in FIG. 2, although the cooling of irradiated points is performed with minimal space defined between the irradiated points, the laser beam irregularly irradiates the skin, so positions in which wrinkles are not smoothed may occur, and skin burns may be caused due to the phenomenon of the laser beam focused on a specific position.

In such a method, the laser beam transmitted from the laser scanner irradiates the skin while forming irregular patterns. The principle of the method is that space between irradiated points is defined, and the cooling time of an earlier irradiated point is secured during the next irradiation.

That is, in forming irradiated points, a laser beam is emitted to be located far from an earlier irradiated point. When the laser beam is repeatedly emitted in such an irregular pattern, another laser beam may irradiate an earlier irradiated point before the earlier irradiated point is cooled. Accordingly, decreasing PIH and DT is difficult, and a wrinkle reduction effect is lowered due to an anatomical structure and inconsistency of the patterns during the enlargement of the skin when the laser beam is emitted in such a pattern. Furthermore, the risk of topical skin burns is increased by repeated irradiation of the laser beam on a specific position due to excessive irregularity of irradiated points.

To solve the above problems, a method of emitting a laser beam in the form of a spot is used, and in this case, a plurality of laser beam spots (micro laser beam spots) is formed.

In the method of treating the skin by emitting the laser beam in the form of a spot, a tiny treatment area is formed, and an energy is transmitted up to a predetermined penetration depth, but aftereffect is required to be reduced, compared to the treatment.

DOCUMENTS OF RELATED ART (Patent Document 1) Korean Patent No. 10-0820164
(Patent Document 2) Korean Patent No. 10-0698868

SUMMARY OF THE INVENTION

Accordingly, the present invention has been made keeping in mind the above problems occurring in the related art, and the present invention is intended to propose a medical skin wrinkle reduction device using an RRSS laser irradiation method, wherein in the skin treatment process of irradiating the skin with a laser, the cooling time and maximum cooling of irradiated points by defining space therebetween through the regular irradiation of the laser beam and a regular pattern formed thereby are secured, whereby wrinkles are evenly smoothed throughout the treatment area, and a predetermined interval between the regular irradiated points is maintained, so that topical skin burns are prevented.

In addition, the present invention is intended to propose a medical skin wrinkle reduction device using an RRSS laser irradiation method, which is provided with an algorithm that to maintain a laser beam at a 90 degree angle to the irradiated surface of the skin for the maximization of the efficiency of skin shrinkage in consideration of the irregularity of the real skin which is enlarged 2,000 times, a random irradiation method is individually applied, and to realize the uniformity and maximization of the shrinkage of the overall skin, a regular irradiation method is collectively applied, whereby the reduction of skin wrinkles can be maximized.

Furthermore, the present invention is intended to propose a medical skin wrinkle reduction device using an RRSS laser irradiation method, wherein a laser pattern part allows regular irradiated points to be formed so that heat energies do not overlap each other when energies of a laser beam are changed to the heat energies inside the dermis, so that tissue damage is minimized.

In order to achieve the above objectives, according to one aspect of the present invention, there is provided a medical skin wrinkle reduction device using an RRSS laser irradiation method, the device including: a main body having a mounting groove provided in an upper portion thereof, a tablet computer being attached to and detached from the mounting groove, and comprising signal transmission and reception parts exchanging signals with the tablet computer, and a microcomputer controlling an output of a laser beam; a handpiece comprising: a laser oscillation part generating the laser beam to be emitted for skin treatment; an optical part emitting the laser beam generated by the laser oscillation as parallel light; a laser scanner controlling an irradiation position of the laser beam transmitted from the optical part; a laser pattern part having movement coordinate values set therein such that moving direction of the laser beam emitted within an outer boundary line for a treatment area recalled from a treatment area display part has a regular pattern; a tablet computer having functions of inputting data in a touch screen method and displaying a screen, and remotely controlling the main body through transmission and reception of two-way signals, wherein in a skin treatment process in which the microcomputer allows the laser beam to be emitted on a skin by using a peak value of a laser pulse while cooling time and maximum cooling of points irradiated by the laser beam are secured due to space defined therebetween when an amplitude of the laser pulse which is generated reaches a preset normal state value of the laser pulse after reaching the peak value, the cooling time of the irradiated points is secured to reduce post-inflammatory hyperpigmentation (PIH) and delayed tanning (DT), and the laser beam is prevented from being repeatedly irradiating a specific position, so that topical skin burns are prevented.

The microcomputer may include: a normal state setting part setting a normal state amplitude of the laser pulse; a pulse transmission time setting part controlling a transmission time of the laser pulse; a pulse width controller controlling a time width of the laser pulse so that generation of the laser pulse stops when the amplitude of the laser pulse reaches the preset normal state value after reaching the peak value; and a laser pulse amplitude controller controlling intensity of laser irradiation by controlling the amplitude of the pulse.

The laser pattern part may allow the irradiated points to be formed maximally in a diagonal direction to make an interval between the irradiated points large, allow the irradiated points to be regularly formed throughout the treatment area, and allow the regular irradiated points to maintain predetermined intervals therebetween, so that skin burns are prevented to minimize tissue damage.

Since the cooling time and maximum cooling are secured due to the pattern of the regular irradiated points, an on-time of the laser beam at each of the irradiated points may be the same, an off-time of the laser beam may be T1 between each irradiated point located in the diagonal direction in which the interval between the irradiated points is large, the off-time of the laser beam may be T2 between each irradiated point located in a horizontal direction, and the off-time of the laser beam may be T3 at a center thereof (here, T1<T2<T3).

The handpiece may include: a rubber clamp having an upper cover case and a lower cover case provided in an outer surface thereof, the upper cover case and the lower cover case being separated from and combined with each other, and protecting the laser oscillation part by covering the laser oscillation part; the laser scanner coupled to an end of the rubber clamp and controlling the irradiation position of the laser beam; the optical part configured as a plurality of parallel light lenses, the optical part emitting the laser beam guided by the laser scanner with the parallel light; the laser pattern part preventing the laser beam from repeatedly irradiating a specific position due to the regular movement pattern in which the laser beam for treatment moves; and a handpiece tip coupled to an end of the optical part and allowing the skin and the optical part to be spaced apart by a predetermined distance from each other.

The microcomputer may be provided with an algorithm that to maintain the laser beam at a 90 degree angle to an irradiated surface of the skin for maximizing efficiency of skin shrinkage in consideration of irregularity of the skin which is enlarged, the laser beam may be emitted in a random method, and to realize uniformity and maximization of overall skin shrinkage, a regular irradiation method may be applied.

The device of the present invention may include the main body generating a laser beam for marking a treatment area and a laser beam for skin treatment according to an input value set by a user; and the handpiece connected to the main body by a light cable, and receiving and irradiating the generated laser beam directly on a skin treatment area, wherein the main body may receive the input value by exchanging signals with the tablet computer and performs wired and wireless control. The medical skin wrinkle reduction method of the present invention may include: the step of setting the output value of the laser beam irradiating the treatment area according a patient's skin condition; the step of setting the transmission time of the laser beam for a pulse signal; the step of setting the resting time of the laser beam for a pulse signal; the step of emitting the laser beam for marking a treatment area on any one of various outer boundaries; the step of recalling the pattern of the regular points irradiated by the laser beam for marking a treatment area; and the step of regularly emitting the laser beam for skin treatment by securing the cooling time and maximum cooling of the irradiated points due to space defined therebetween due to the pattern of the regular irradiated points.

While the cooling time and maximum cooling of the irradiated points due to the space defined therebetween due to the pattern of the regular irradiated points are secured, the on-time of a laser beam of each irradiated point may be the same, and the off-time of the laser beam may be T1 between each irradiated point located in a diagonal direction in which an interval between each irradiated point is large, the off-time of the laser beam may be T2 between each irradiated point located in a horizontal direction, and the off-time of the laser beam may be T3 at the center thereof.

According to the present invention, in the skin treatment process of emitting a laser beam on the skin using the RRSS laser irradiation method for reducing skin wrinkles and minimizing tissue damage, the cooling of the irradiated points defined in a predetermined pattern is maximized by securing the cooling time and maximum cooling of the irradiated points due to space defined therebetween, whereby topical skin burns are prevented.

In addition, according to the present invention, the laser beam is prevented from repeatedly irradiating a specific position due to the regular irradiation of laser beam, whereby the topical skin burns are prevented from occurring, and the wrinkles of the skin are evenly smoothed throughout the treatment area.

Furthermore, according to the present invention, provided is an algorithm that to maintain a laser beam at a 90 degree angle to the irradiated surface of the skin for the maximization of the efficiency of skin shrinkage in consideration of the irregularity of the real skin which is enlarged 2,000 times, a random irradiation method is individually applied, and to realize the uniformity and maximization of the shrinkage of overall skin, a regular irradiation method is collectively applied, whereby the reduction of skin wrinkles can be maximized.

In addition, in the present invention, a peak value of the laser pulse is used to treat skin by the pulse width controller controlling the time width of the laser pulse, and by the normal state setting part setting the normal state amplitude of the laser pulse.

Furthermore, in the present invention, a therapist's misunderstanding and confusion about the output level of a laser beam are prevented due to a lamp for indicating the output level of a laser beam lighted in different colors according to the output level of laser beam.

BRIEF DESCRIPTION OF THE DRAWINGS

The above and other objectives, features, and other advantages of the present invention will be more clearly understood from the following detailed description when taken in conjunction with the accompanying drawings, in which.

DETAILED DESCRIPTION OF THE INVENTION

Figure 1:
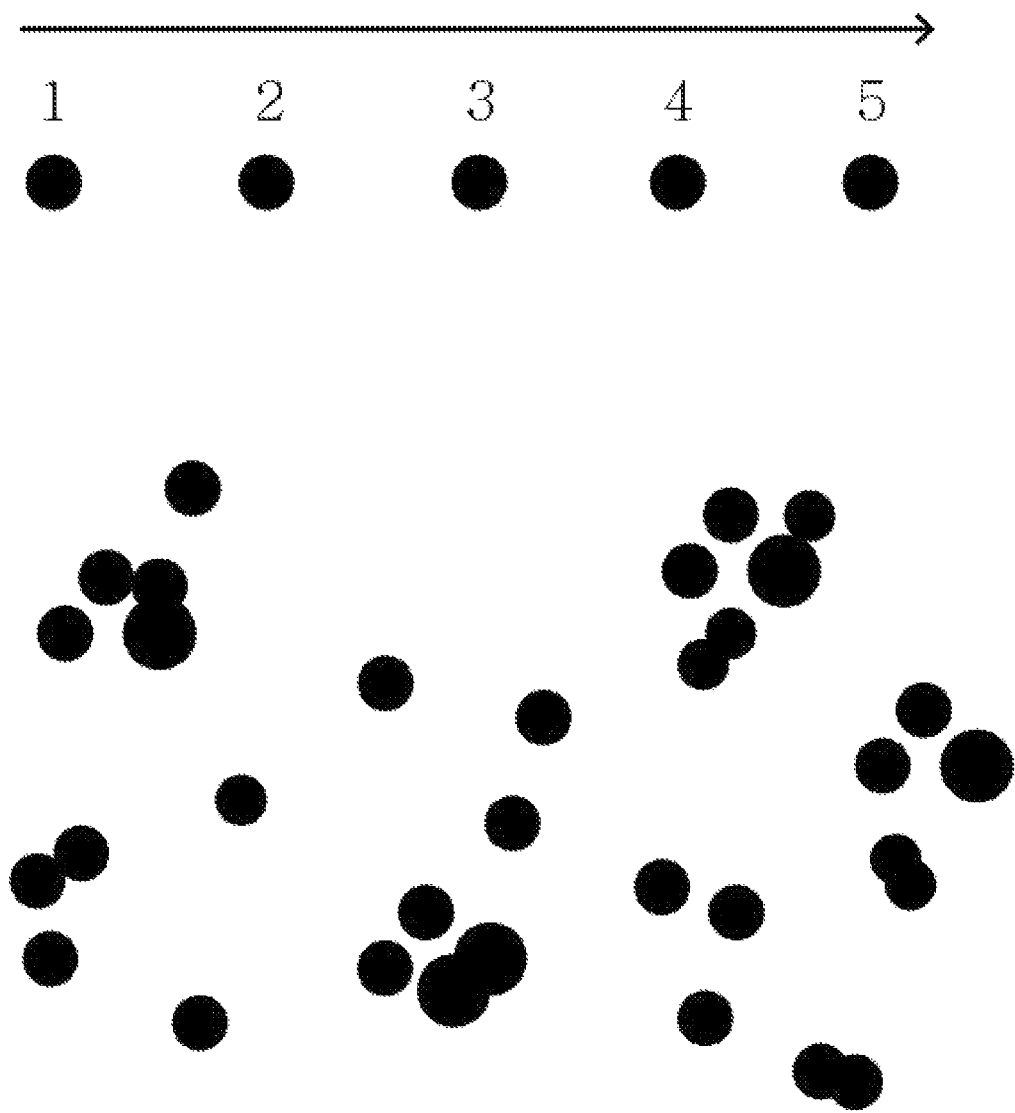
FIG. 1 illustrates the pattern of irradiated points formed by a conventional laser.
Figure 2:
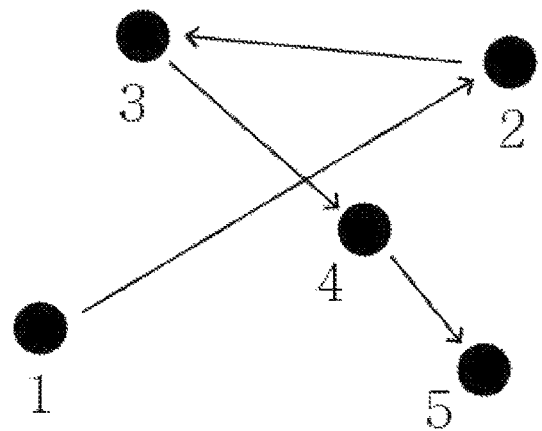
FIG. 2 illustrates the pattern of irradiated points formed by another conventional laser.
Figure 2:
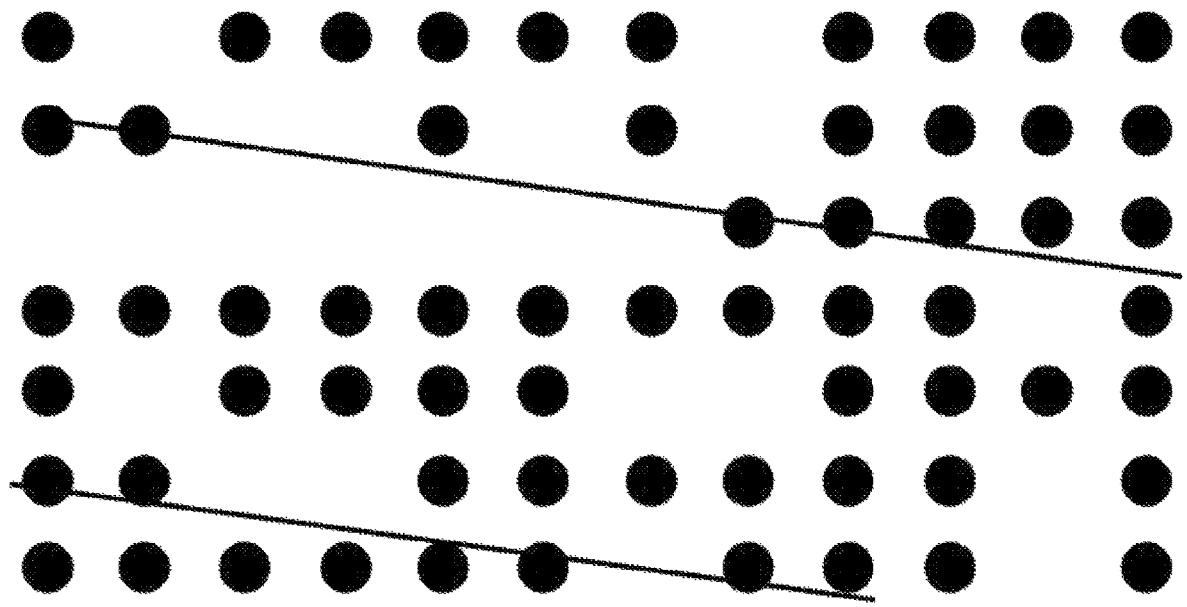

In order to fully understand the present invention, an exemplary embodiment of the present invention will be described with reference to the accompanying drawings. The embodiment of the present invention may be modified in various forms, and it should not be interpreted that the scope of the present invention is limited to the embodiment described in detail below.

This embodiment is provided to more fully explain the present invention to those skilled in the art. Therefore, the shape of elements in the drawings may be exaggerated to emphasize a clearer description.

It should be noted that in each drawing, the same members may be indicated by the same reference numerals. In addition, detailed descriptions of well-known functions and configurations that are judged to unnecessarily obscure the subject matter of the present invention are omitted.

Figure 3A:
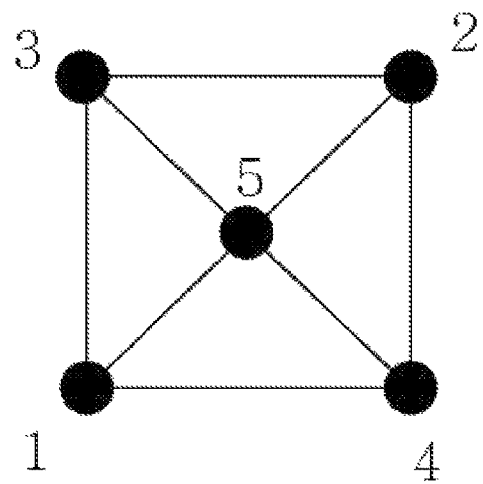
FIG. 3A illustrates a pattern formed in an RRSS laser irradiation method according to an embodiment of the present invention.
Figure 3A:
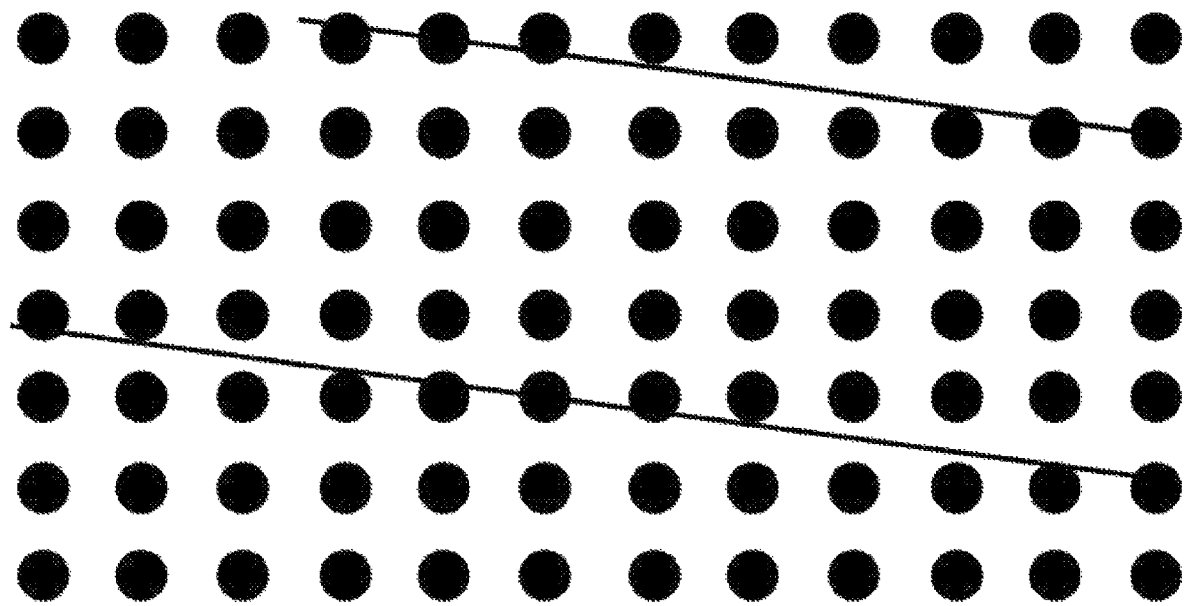
Figure 3B:
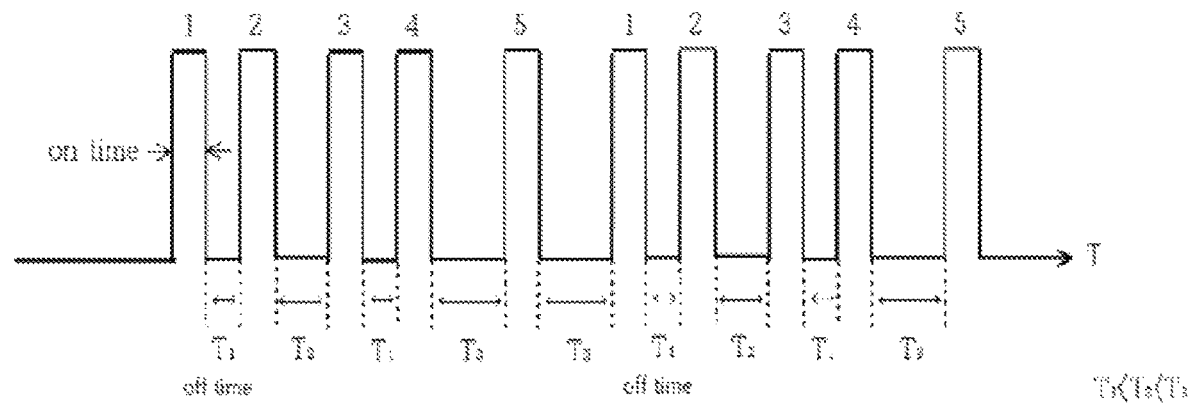
FIG. 3B illustrates the on-time (transmission time) and the off-time (resting time) of a laser pulse.

FIG. 3A illustrates a pattern formed in an RRSS laser irradiation method according to an embodiment of the present invention, and FIG. 3B illustrates the on-time (transmission time) and off-time (resting time) of a laser pulse.

As illustrated in FIG. 3A, the pattern of points irradiated by a laser beam is formed in the RRSS laser irradiation method for minimizing tissue damage. The regular irradiation is performed with the irradiated points being spaced apart by an predetermined interval from each other without the phenomenon of the laser beam focused on a specific position by securing the cooling time and maximum cooling of the irradiated points due to space defined therebetween due to the regular irradiation of laser beam, so that skin wrinkles are evenly smoothed throughout the treatment area, and skin burns are prevented.

As an embodiment, as for the pattern of regular points irradiated by a laser beam, a laser beam is emitted on a bottom left (a number 1); is emitted on an upper right (a number 2) in a direction diagonal thereto by increasing an interval therebetween; is emitted on an upper left (a number 3) in a direction horizontal thereto, is emitted on a lower right (a number 4) in a direction diagonal thereto, and is emitted on a center (a number 5) thereof, so that a pattern is completed. In succession, while the laser beam is constantly moving in rows or columns, the patterns of the regular irradiated points are repeatedly generated.

As illustrated in FIG. 3B, the cooling time and maximum cooling of the irradiated points due to space defined therebetween due to the pattern of the regular irradiated points are secured. Accordingly, the on-time of the laser beam at each irradiated point is the same, and the off-time of the laser beam is T1 between each irradiated point located in a diagonal direction having a large interval between each irradiated point, and the off-time of the laser beam is T2 between each irradiated point located in a horizontal direction, and the off-time of the laser is T3 at the center thereof (here, $T1<T2<T3$).

That is, the off-time of the laser beam is short in a diagonal direction in which an interval between the irradiated points is large, and as the interval between the irradiated points decreases, the off-time of the laser beam increases.

When the laser beam is emitted while moving in rows and columns in this way, the irradiated points are regularly formed as illustrated in FIG. 3A, and these irradiated points are formed while being maintained to be spaced apart at predetermined intervals from each other. Accordingly, since the regular irradiation of the laser beam is performed by securing the cooling time and maximum cooling of the irradiated points by defining space therebetween with the predetermined interval maintained between the irradiated points, the wrinkles of the skin are evenly smoothed throughout the treatment area. Furthermore, since the laser beam is not focused on a specific position, there is little possibility of skin burns.

Figure 3C:
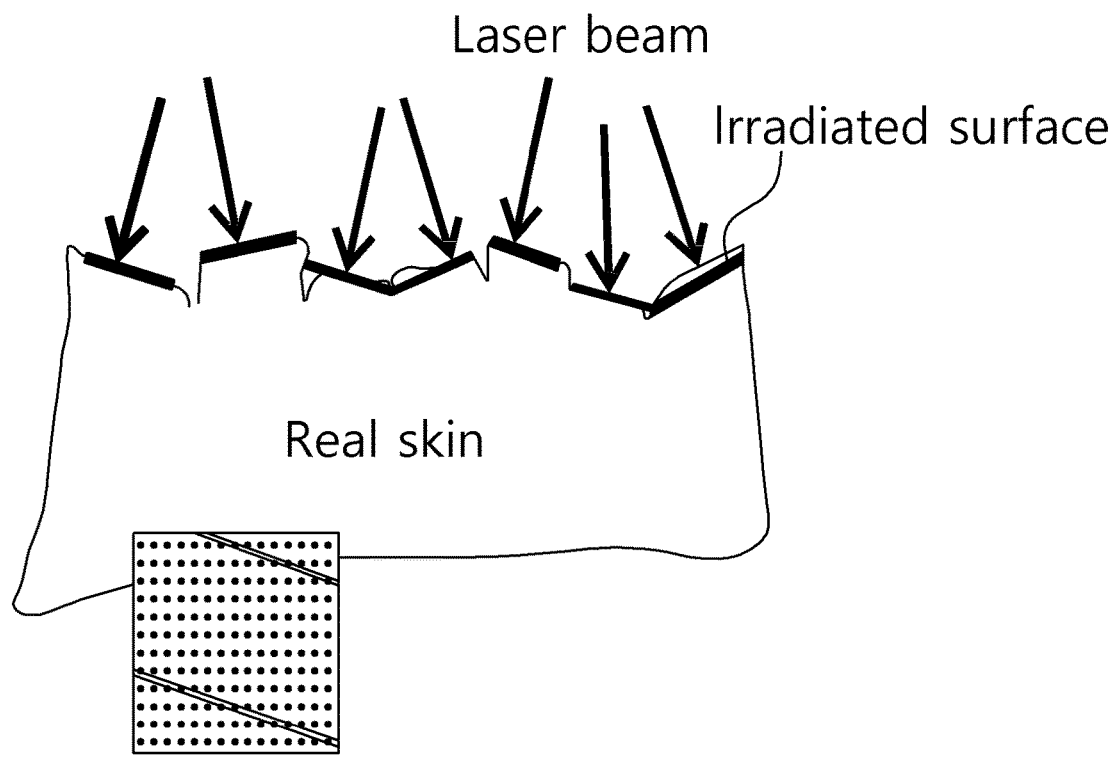
FIG. 3C is a view illustrating laser beams emitted at an angle orthogonal to a skin surface according to the embodiment of the present invention.

In addition, FIG. 3C is a view illustrating laser beams emitted at an angle orthogonal to a skin surface according to the embodiment of the present invention.

As illustrated in FIG. 3C, wrinkles are caused by the stretching of the skin, so the wrinkles are reduced when the skin shrinks. When the laser beam irradiates the skin tissue by using the peak value of the laser pulse, the skin shrinks due to the heat of the laser beam.

In this case, when the laser beam irradiates the surface of the skin orthogonally, the efficiency of skin shrinkage is maximized. Accordingly, in the method of using the RRSS laser irradiation method according to the present invention, provided is an algorithm that to maintain a laser beam at a 90 degree angle to the irradiated surface of the skin for the maximization of the efficiency of skin shrinkage in consideration of the irregularity of the real skin which is enlarged 2,000 times, a random irradiation method is individually applied, and to realize the uniformity and maximization of the shrinkage of overall skin, a regular irradiation method is collectively applied.

That is, to irradiate the laser beam orthogonally to the irradiated surface of the skin in consideration of the irregularity of the real skin, the random irradiation method is individually applied to maximize the efficiency of the shrinkage and wrinkle reduction of a partial skin, and to realize the uniformity and maximization of the shrinkage of overall skin, the regular irradiation method is collectively applied so that the reduction of skin wrinkles is efficiently performed.

Figure 4:
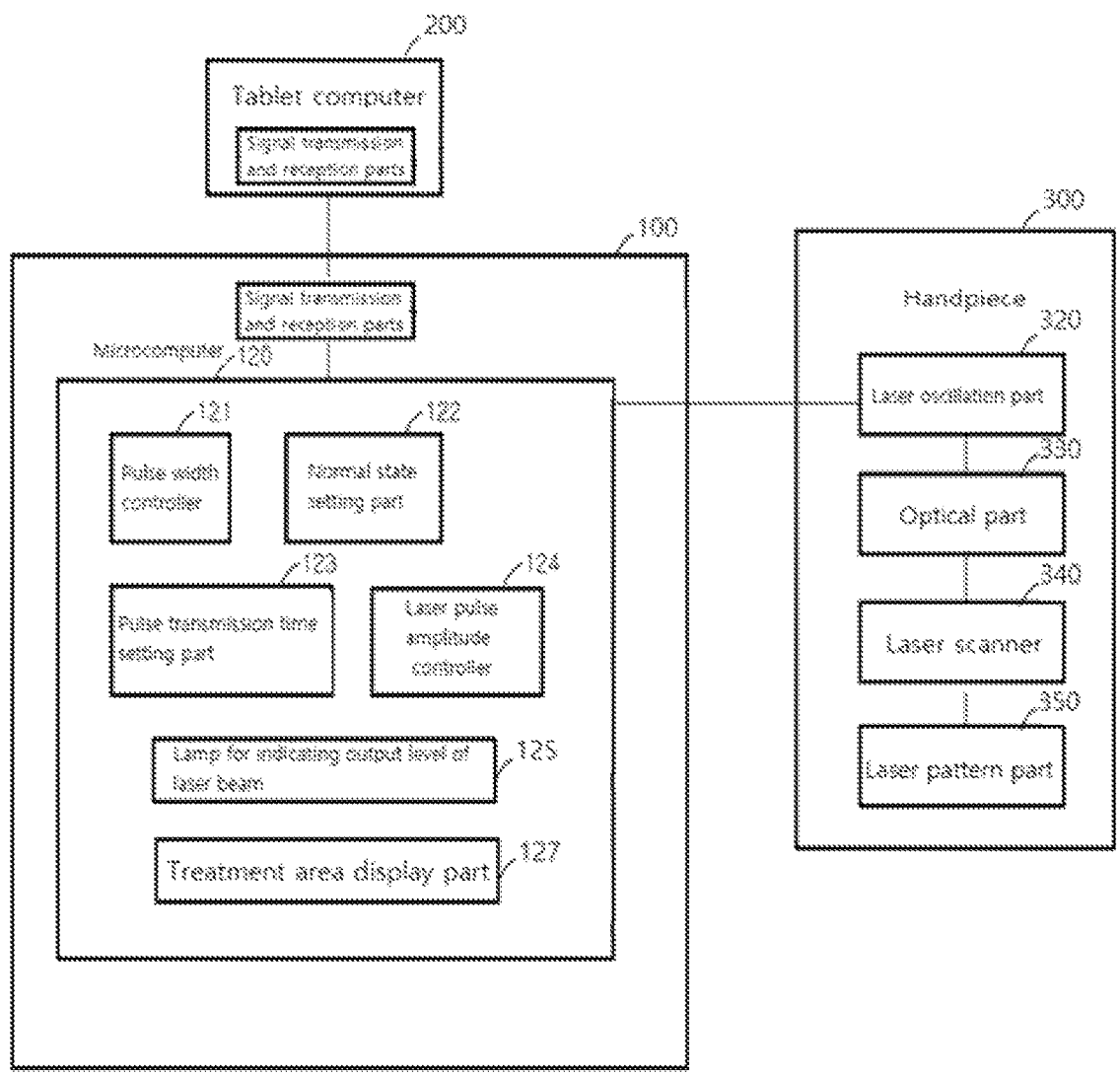
FIG. 4 is a block diagram of a medical skin wrinkle reduction device using the RRSS laser irradiation method according to the embodiment of the present invention.

FIG. 4 is a block diagram of a medical skin wrinkle reduction device using the RRSS laser irradiation method according to the embodiment of the present invention.

As illustrated in FIG. 4, a microcomputer 120 of the present invention controls a handpiece 300 and a tablet computer 200. The microcomputer 120 is provided with a pulse width controller 121, a normal state setting part 122, a pulse transmission time setting part 123, a pulse amplitude controller 124, and a lamp 125 for indicating the output level of a laser beam so that various design parameters for the laser pulse are controlled.

The microcomputer 120 of the present invention allows a laser beam to irradiate the skin tissue by using the peak value of the laser pulse when the amplitude of generated laser pulse reaches a preset normal state value of the laser pulse after reaching the peak value.

The treatment is performed by increasing the transmission time of a laser beam per unit time when the peak value of the laser pulse is used compared to when the normal state value of the laser pulse is used.

To this end, the microcomputer 120 is provided with the pulse transmission time setting part 123 controlling the transmission time of the laser pulse.

In addition, the device of the present invention is provided with the laser pulse amplitude controller 124 controlling the amplitude of the laser pulse so as to control the intensity of laser irradiation.

Furthermore, the microcomputer 120 includes the lamp 125 for indicating the output level of a laser beam. The lamp 125 is lighted in different colors according to the output level of the laser beam to prevent a therapist's misunderstanding and confusion about the output level of the emitted laser beam.

A treatment area display part 127 stores an outer boundary line for a patient's treatment area preset in various forms, which may include forms set randomly by a user.

Such an outer boundary line for the treatment area is required to preset the scope of the treatment for forming tiny holes in skin tissue by using the peak value of the laser pulse.

A main body 100 includes the mounting groove 110 provided therein, the tablet computer 200 attached thereto and detached therefrom, and includes the microcomputer 120 controlling the handpiece 300 and the tablet computer.

The handpiece 300 is a device that directly emits the laser beam by approaching a patient's treatment area, and is connected to the main body 100 by an optical cable. The handpiece 300 includes: a laser oscillation part (e.g., laser oscillator) 320 generating a laser beam to be emitted for skin treatment; an optical part 330 emitting the laser beam generated by the laser oscillation part 320 as parallel light; a laser scanner 340 controlling the irradiation position of the laser beam transmitted from the optical part 330; and a laser pattern part 350 having movement coordinate values set therein so that the moving direction of the laser beam emitted within the outer boundary line for the treatment area recalled from the treatment area display part has a regular pattern.

The handpiece 300 further includes: a rubber clamp 310 having an upper cover case and a lower cover case combined with each other in an outer surface thereof, and protecting the laser oscillation part 320 by covering the laser oscillation part; and a handpiece tip 370 coupled to an end of the optical part 330, and allowing the skin and the optical part 330 to be spaced apart by a predetermined distance from each other.

The laser oscillation part 320 of the present invention includes an Erbium glass laser. The Erbium glass laser is a device that generates a laser beam irradiating the patient's treatment area, and uses the peak value of the laser pulse to form a tiny hole in the skin tissue.

The optical part 330 is a device emitting the laser beam generated by the laser oscillation part 320 as the parallel light. The optical part 330 having parallel correction lenses applied thereto outputs the parallel light after generating the parallel light.

The laser scanner 340 functions to control the coordinates of positions irradiated by the laser beam when the laser beam transmitted from the optical part 330 irradiates the patient's treatment area.

That is, the laser scanner includes an X-axis rotation mirror, an X-axis control motor controlling the angle of the X-axis rotation mirror, a Y-axis rotation mirror, and a Y-axis control motor controlling the angle of the Y-axis rotation mirror. Accordingly, the laser scanner can change the coordinates of the laser beam irradiating the treatment area.

In forming a tiny hole in a skin tissue for the treatment area, the laser pattern part 350 sets and stores the movement coordinate values so that the moving direction of the laser beam irradiating the treatment area within the outer boundary line for the treatment area recalled from the treatment area display part 127 has the regular pattern.

The regular movement pattern of the laser beam for skin treatment reduces the concern that the laser beam repeatedly irradiates a specific position. Due to this regular movement pattern, the laser beam regularly irradiates the skin, and the cooling efficiency of the skin is improved, so that the wrinkles of the skin is evenly smoothed throughout the treatment area, and skin burns are prevented at specific positions.

In the tablet computer 200, the function of inputting data and displaying a screen in the touch screen method can be embodied, and various set values for laser transmission can be input and the progress of the laser transmission can be displayed.

In addition, the tablet computer 200 has CPU and memory provided therein, and has the function of calculating and storing data. The tablet computer 200 is configured to be attached to and detached from the mounting groove 110 of the main body 100, thereby enabling portability and mobility for the tablet computer 200 or the main body 100. The tablet computer 200 also has signal transmission and reception parts to exchange signals with the signal transmission and reception parts of the main body 100, as shown in FIG. 4.

Figure 5:
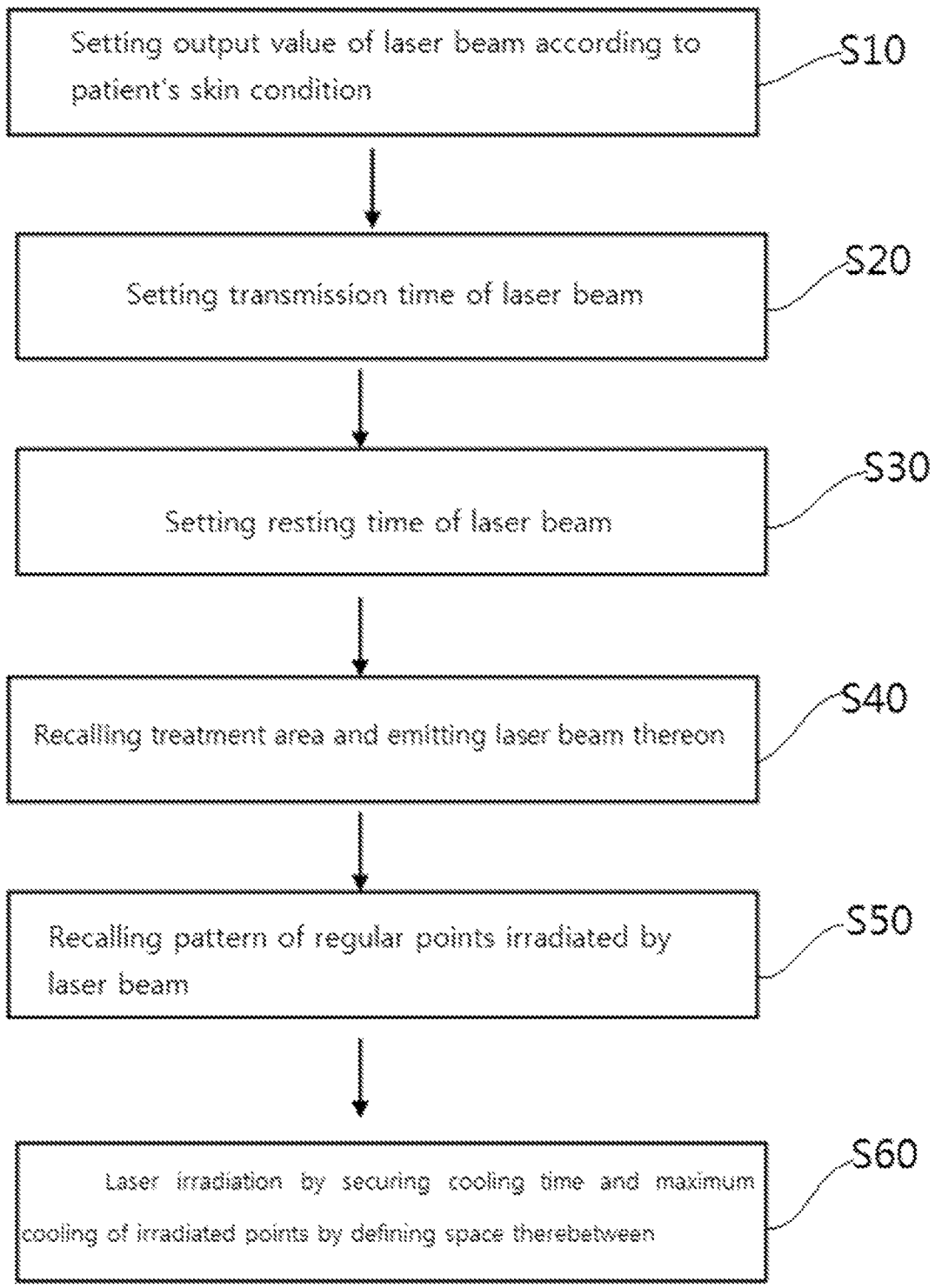
FIG. 5 is a flow chart of a medical skin wrinkle reduction method using the RRSS laser irradiation method according to the embodiment of the present invention.
Figure 6:
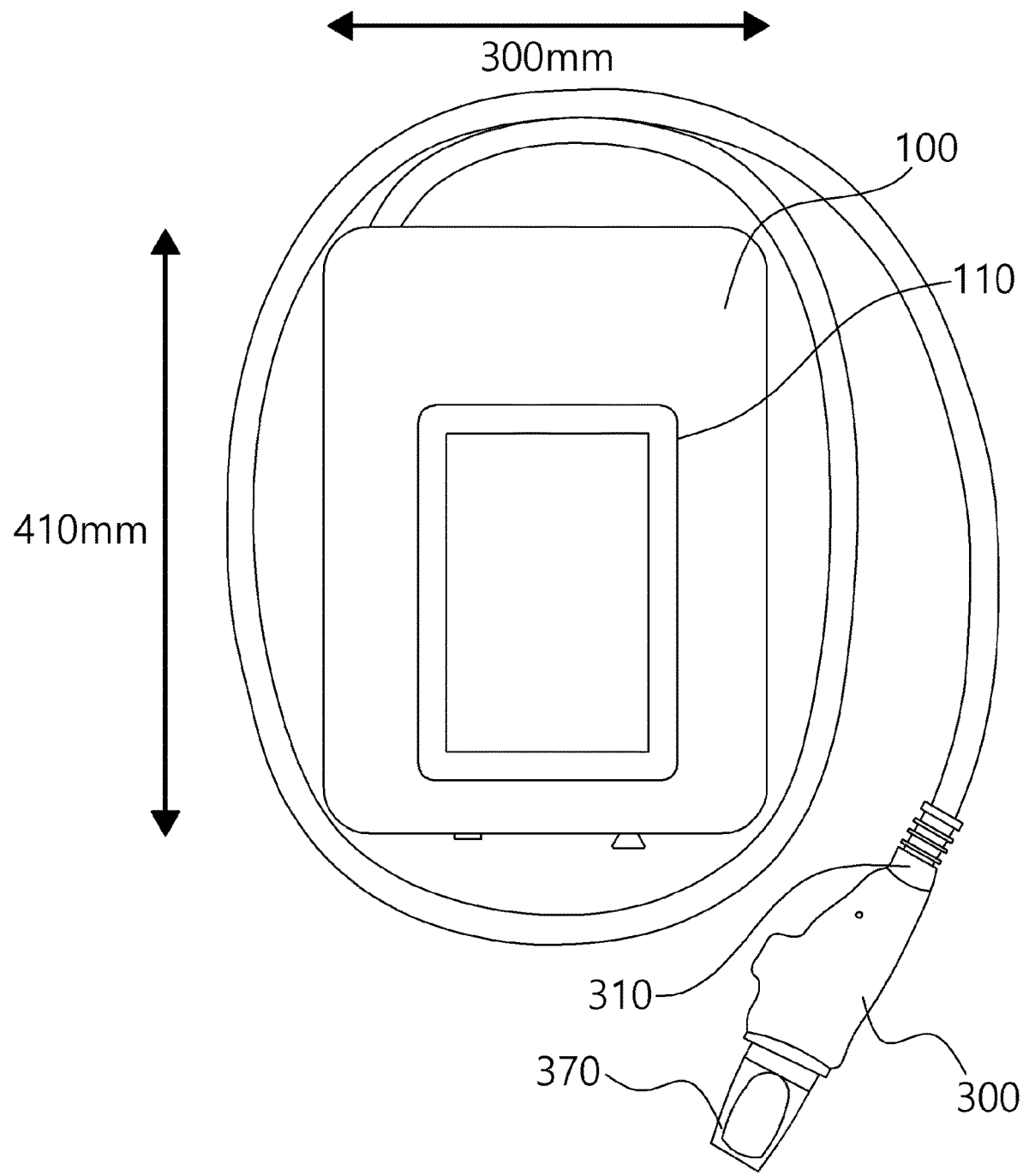
FIG. 6 is a product picture of the medical skin wrinkle reduction device using the RRSS laser irradiation method of the present invention.

FIG. 5 is a flow chart of a medical skin wrinkle reduction method using the RRSS laser irradiation method according to the embodiment of the present invention.

As illustrated in FIG. 5, the medical skin wrinkle reduction method using the RRSS laser irradiation method for minimizing tissue damage according to the present invention includes 1) the step of setting the output value of the laser beam→2) the step of setting the transmission time of the laser beam→3) the step of setting the resting time of the laser beam→4) the step of recalling a treatment area and emitting a laser beam for marking the treatment area thereon→5) the step of recalling the pattern of the regular points irradiated by a laser beam→6) the step of emitting the laser beam for skin treatment while securing cooling time and maximum cooling of the irradiated points.

1) The step S10 of setting the output value of a laser beam.

The wavelength value of the laser beam irradiating the treatment area according to the patient's skin condition is set, the transmission time of the laser beam continuously transmitted at a time during the transmission of the laser beam is set, and the energy density of the laser beam is set.

2) The step S20 of setting the transmission time of a laser beam.

Setting the transmission time of the laser beam is performed by considering a patient's skin condition for the irradiation positions of the laser beam. The laser beam irradiates the treatment area by appropriate controlling of the transmission time thereof, whereby the cooling time of the skin is secured, and topical skin burns are prevented.

3) The step S30 of setting the resting time of a laser beam.

The laser beam irradiates the treatment area in the pattern of the regular irradiated points by securing the cooling time and maximum cooling of the irradiated points by defining space therebetween. The on-time of the laser beam at each of the irradiated points is the same. The off-time of the laser beam is T1 between each irradiated point located in the diagonal direction in which an interval between the irradiated points is large, the off-time of the laser beam is T2 between each irradiated point located in a horizontal direction, and the off-time of the laser beam is T3 at the center thereof (here, T1<T2<T3).

That is, the off-time of a laser beam is short in a diagonal direction in which an interval between the irradiated points is large, and as the interval between the irradiated points decreases, the off-time of the laser beam is set to be long, whereby the cooling time of the skin is secured, and topical skin burns are prevented.

4) The step S40 of recalling the treatment area and emitting a laser beam thereon.

Before irradiating a patient's skin for treatment by using the peak value of the laser pulse, the laser beam for marking the treatment area irradiated within the outer boundary line is used to mark a patient's skin treatment area. In this case, the shape of the outer boundary line is recalled so as to be applied to the treatment area. The recalled shape of the outer boundary line is set, and is applied to the treatment area.

5) The step S50 of recalling the pattern of the regular points irradiated by a laser beam.

The movement pattern in which the laser beam irradiates a patient's skin within the outer boundary line by using the peak value of the laser pulse is recalled. The movement pattern is regularly formed, so the laser beam is prevented from repeatedly irradiating a specific position.

6) The step S60 of emitting the laser beam for skin treatment while securing the cooling time and maximum cooling of the irradiated points.

The laser beam irradiates the skin treatment area of a patient by using the peak value of the laser pulse, tiny holes are formed in skin tissue, and the corresponding portions are treated. Accordingly, the treated portions are regenerated, and thus the treatment effect of the skin is obtained. According to the present invention, the laser beam irradiates the treatment area by being moved in the regular movement pattern.

In the above, the technical idea of the present invention has been described with reference to the accompanying drawings, but this is an exemplary description of the best embodiment of the present invention, and is not intended to limit the present invention.

In addition, it is obvious that anyone with ordinary knowledge in this technical field can make various modifications and imitation without departing from the scope of the technical idea of the present invention.

What is claimed is:

1. A device for reducing skin wrinkles by a regular laser irradiation, the device comprising:
a main body having a mounting groove for a tablet computer to be attached to and detached from the mounting groove, wherein the main body is configured for exchanging signals with the tablet computer and includes a microcomputer for controlling an output of a laser beam; and
a handpiece connected to the main body by an optical cable,
wherein the handpiece includes:
a laser oscillator generating the laser beam to be emitted for skin treatment;
a plurality of light lenses configured for emitting the laser beam generated by the laser oscillator; and
a laser scanner controlling an irradiation position of the laser beam transmitted from the plurality of light lenses, and having movement coordinate values set therein such that a moving direction of the laser beam to be emitted within an outer boundary line of a treatment area has a regular pattern;
wherein the tablet computer is configured for receiving input data through a touch screen and remotely controlling the main body through transmission and reception of two-way signals,
wherein the microcomputer is configured to control the laser beam to be emitted on a skin by using a peak value of a laser pulse while cooling time and maximum cooling of points irradiated by the laser beam are secured due to a space defined therebetween when an amplitude of the laser pulse reaches a preset normal state value of the laser pulse after reaching the peak value,
wherein the cooling time of the irradiated points is secured to reduce post-inflammatory hyperpigmentation (PIH) and delayed tanning (DT), and
wherein the laser beam is prevented from being repeatedly irradiated to a specific position, so that topical skin burns are prevented,
wherein the microcomputer controls the laser scanner to allow the irradiated points to be spaced to form a square including five points in which four points define vertices of the square and the fifth point is in a center of the square, allow the irradiated points to be regularly and repeatedly formed throughout the treatment area, and allow the regular irradiated points to maintain predetermined intervals therebetween, so that skin burns are prevented to minimize a tissue damage, wherein the microcomputer is configured to control irradiation time of the laser beam such that on-time of the laser beam at each of the irradiated points is equal to each other, and wherein, when a first off-time of the laser beam between two irradiated points spaced apart in a diagonal direction in the square is T1, a second off-time of the laser beam between two irradiated points spaced apart in a horizontal direction in the square is T2, and a third off-time of the laser beam at a center of the two irradiated points spaced apart in the diagonal direction is T3, the microcomputer is configured to control such that the first off-time (T1) is less than the second off-time (T2) and the second off-time (T2) is less than the third off-time (T3).

2. The device of claim 1, wherein the microcomputer is configured for:
   setting a normal state amplitude of the laser pulse;
   controlling a transmission time of the laser pulse;
   controlling a time width of the laser pulse so that generation of the laser pulse stops when the amplitude of the laser pulse reaches the preset normal state value after reaching the peak value; and
   controlling intensity of laser irradiation by controlling the amplitude of the pulse.

3. The device of claim 1, wherein the handpiece further comprises:
   a rubber clamp having an upper cover case and a lower cover case disposed in an outer surface thereof, the upper cover case and the lower cover case being separated from or combined with each other, and protecting the laser oscillator by covering the laser oscillator; and
   a handpiece tip disposed at an end of the handpiece and configured for allowing the skin and the plurality of light lenses to be spaced apart by a predetermined distance from each other,
   wherein the laser scanner is coupled to an end of the rubber clamp and controlling the irradiation position of the laser beam,
   wherein the plurality of light lenses are configured for emitting the laser beam in parallel, and
   wherein the laser scanner is configured for preventing the laser beam from repeatedly irradiating to the specific position due to a regular movement pattern along which the laser beam for treatment moves.

4. The device of claim 1, wherein the microcomputer is configured to control the laser beam to be directed at a 90-degree angle to an irradiated surface of the skin for maximizing efficiency of skin shrinkage.

* * * * *